United States Patent
Datla et al.

(10) Patent No.: US 12,358,871 B2
(45) Date of Patent: Jul. 15, 2025

(54) PHOTOCHEMICAL SYNTHESIS OF VITAMIN D3 USING SENSITIZERS

(71) Applicant: FERMENTA BIOTECH LIMITED, Thane (IN)

(72) Inventors: Anupama Datla, Thane (IN); Prashant Nagre, Thane (IN); Jagdish Tamore, Thane (IN); Sreenath Trivikram, Dombivli (IN); Gajanan Degaonkar, Badlapur (IN)

(73) Assignee: FERMENTA BIOTECH LIMITED, Thane (IN)

( * ) Notice: Subject to any disclaimer, the term of this patent is extended or adjusted under 35 U.S.C. 154(b) by 924 days.

(21) Appl. No.: 17/608,931

(22) PCT Filed: May 5, 2020

(86) PCT No.: PCT/IN2020/050442
§ 371 (c)(1),
(2) Date: Nov. 4, 2021

(87) PCT Pub. No.: WO2020/230169
PCT Pub. Date: Nov. 19, 2020

(65) Prior Publication Data
US 2022/0298106 A1    Sep. 22, 2022

(30) Foreign Application Priority Data
May 15, 2019    (IN) .............................. 201921019395

(51) Int. Cl.
*C07C 401/00*    (2006.01)

(52) U.S. Cl.
CPC .................................. *C07C 401/00* (2013.01)

(58) Field of Classification Search
None
See application file for complete search history.

(56) References Cited

U.S. PATENT DOCUMENTS

| 4,686,023 A | 8/1987 | Stevens |
| 5,252,191 A | 10/1993 | Pauli et al. |
| 7,211,172 B1 | 5/2007 | Saltiel |

FOREIGN PATENT DOCUMENTS

CN    101830840 A    *    9/2010

OTHER PUBLICATIONS

Machine translation on CN101830840A, Sep. 15, 2010, pp. 1-4, (Year: 2010).*
"Continuous-flow synthesis of vitamin D3": Takashi Takahashi et al., Chemical Communications, vol. 46, No. 46: DOI: 10.1039/c0cc02239j; Sep. 28, 2010 (Sep. 28, 2010); pp. 8722-8724.
Written Opinion of The International Searching Authority for Application No. PCT/IN2020/050442 filed May 15, 2020; 4 pages.
International Search Report for Application No. PCT/IN2020/050442 filed May 15, 2020; 2 pages.

* cited by examiner

*Primary Examiner* — Medhanit W Bahta
(74) *Attorney, Agent, or Firm* — Kramer & Amado, P.C.

(57) ABSTRACT

The present invention discloses an improved photochemical synthesis of vitamin D3 from 7-dehydrocholesterol alone or in combination with sterol precursors in presence of the photosensitizer of Formula I in high yield and with reduced levels of impurities.

20 Claims, No Drawings

PHOTOCHEMICAL SYNTHESIS OF VITAMIN D3 USING SENSITIZERS

FIELD OF INVENTION

The present invention relates to improved photochemical synthesis of vitamin D3 from 7-dehydrocholesterol alone or in combination with sterol precursors in presence of the photosensitizer of Formula I in high yield and with reduced levels of contaminants.

BACKGROUND OF THE INVENTION

Cholecalciferol, commonly known as Vitamin D3 is used to treat and prevent vitamin D deficiency and associated diseases, including rickets. Cholecalciferol is taken as a supplement to improve overall health and to treat osteoporosis. Vitamin D3 is produced in the human body through the exposure to UVB light on its provitamin 7-dehydrocholesterol (7-DHC).

Vitamin D3 is fat soluble, is sensitive to moisture, air and light and may react vigorously with strong oxidizing agents. Cholecalciferol does absorb light at wavelengths >290 nm and therefore may be susceptible to direct photolysis by sunlight.

7-Dehydrocholesterol (7-DHC) is a zoosterol that functions in the serum as a cholesterol precursor, and is converted to vitamin D3 in the skin, therefore functioning as provitamin-D3. The presence of this compound in human skin enables humans to manufacture vitamin D3 (cholecalciferol) from ultraviolet rays in the sun light, via an intermediate isomer pre-vitamin D3. The conversion of 7-dehydrocholesterol to vitamin D3 occurs in two steps. In the first step, 7-dehydrocholesterol on irradiation produces previtamin D3 which then spontaneously isomerises to vitamin D3 (cholecalciferol).

U.S. Pat. No. 7,211,172 disclose photochemical method of making vitamin D which includes irradiating a reaction mixture of precursor molecules with light having a wavelength of 254 nm and with light having a wavelength of 313 nm to produce previtamin D and followed by heating at a temperature not exceeding 100° C. to convert previtamin D to vitamin D.

In the traditional process, 7-dehydrocholesterol (Pro-vitamin D3) in ethanol is irradiated using a mercury lamp as a light source for 2-4 hours. The HPLC analysis of the reaction mass indicated the formation of pre-vitamin D3 (85-86%) along with Tachysterol (4.5-6.0%), Lumisterol (1.0-1.5%) and pro-vitamin D3 (1.0-2.0%). The reaction mass is further heated to 40-80° C. for 2-10 hours to yield Crude vitamin D3. Subsequently the crude Vitamin D3 is converted to its ester, crystallized and finally saponified, crystallized to yield Vitamin D3 or Cholecalciferol.

U.S. Pat. No. 4,686,023 discloses photochemical conversion of 7-DHC to previtamin D3 by carrying out the irradiation reaction in the presence of anthracene as a photosensitizer. HPLC analysis indicated the reaction mixture containing pre-vitamin D3 (88-91%), Tachysterol (0.5-1%), Lumisterol (2-3%) and pro-vitamin D3 (7.5-8.5%). The reaction mass is further heated to 50-100° C. for a sufficient length of time to produce vitamin D3. The disadvantage in using anthracene as photosensitizer is that anthracene hydrocarbon is difficult to remove from vitamin D3 which is a laborious process. The conversion of previtamin D3 to vitamin D3 takes a longer period of time to effect the conversion.

The irradiation processes in the art does not produce vitamin D3 in satisfactory yield and purity. Further, in view of the intended use of vitamin D3 for human and veterinary administration it is essential that vitamin D3 produced by irradiation method should be free from all types of contaminants.

Substituted thiophene derivatives are reported as photosensitizer in U.S. Pat. No. 5,252,191 for the photochemical isomerization of tachysterol to previtamin D3. The conversion is carried out in presence of other photosensitizers such as sodium bromide, silver sulphate and mercury sulphate using high pressure mercury lamp as light source.

7-Dehydrocholesterol absorbs UV light most effectively at wavelengths between 290 and 320 nm and the production of vitamin D3 occurs primarily at these wavelengths. The conversion of previtamin D3 to the active form, vitamin D3, involves a rupture of the ring and loss of the true sterol identity. Theoretically, rupture of the sterol ring can lead to 64 different isomers, however, only a few of the isomers occur naturally or are formed during synthesis of vitamin D3. Primarily, the isomers formed during preparation of vitamin D3 by irradiation are tachysterol, lumisterol and trans Vitamin D3.

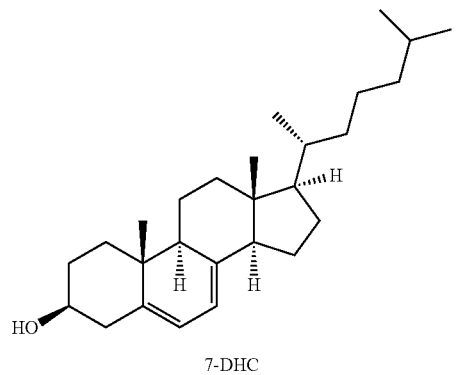

7-DHC

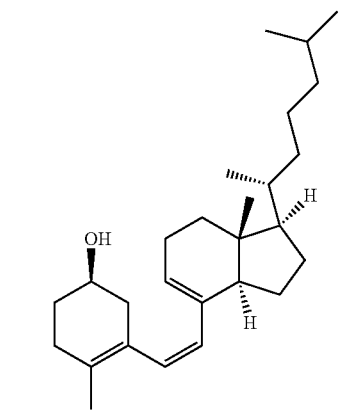

Pre-vitamin D3

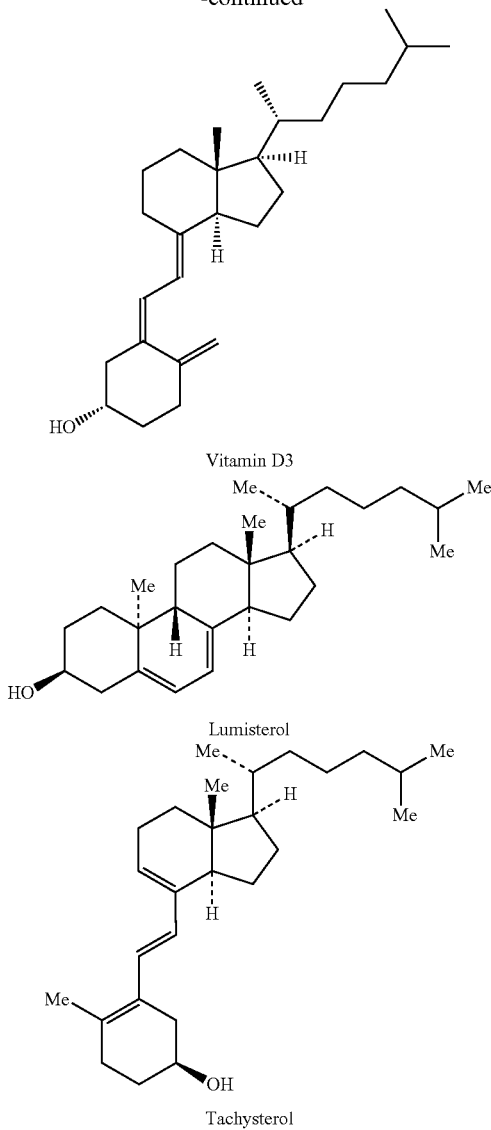

Vitamin D3

Lumisterol

Tachysterol

One reason for low conversion of 7-DHC to vitamin D3 in conventional processes using mercury pressure lamps is that the radiation spectrum produced is not optimized for the 280-300 nm wavelength which results in a large amount of undesired by-products by irradiation outside the optimum wavelength range.

It is therefore necessary in the present state of the art to interrupt the undesired wavelength range radiated by mercury pressure lamps such that it results in the high conversion rate of 7-DHC to previtamin D3 and subsequently to vitamin D3 with reduction in the levels of by-products tachysterol, lumisterol and residual 7-DHC.

The present inventors observed that yield of vitamin D3 is limited by the equilibrium state in the exposure region and over irradiation lead to irreversible stoichiometric losses of the interconverting isomers to undesirable isomers. It was therefore felt to improve the selectivity and yield of vitamin D3 during photochemical synthesis.

The stoichiometric losses of the interconverting isomers to undesirable isomers during photo conversion could be reduced by using animal or plant sourced sterol precursors in combination with 7-DHC and interrupting the undesired wavelength using sensitizers.

It is therefore the objective of the present invention to provide a photochemical synthesis of vitamin D3 from 7-DHC alone or in combination with animal or plant sourced sterol precursors in presence of a photosensitizer with high selectivity, reduced impurity and having high potency.

SUMMARY OF THE INVENTION

To meet the objectives, the present invention provides an improved photochemical conversion of 7-dehydrocholesterol alone or in combination with sterol precursor to Vitamin D3 in high yield and reduced impurity using photosensitizer, of Formula I.

The photosensitizer of Formula I used in the irradiation process of the present invention comprises;

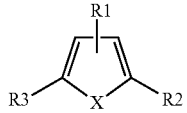

Formula I wherein;
X represents 'O' or 'S';
R1 represents a hydrogen atom or C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S.

The photosensitizer used in the present invention absorbs a substantial portion of the radiation so as to cause the photochemical conversion of 7-DHC to vitamin D3 in high yield and reduced impurities.

In an aspect, the present invention provides improved photochemical synthesis of vitamin D3 with high selectivity and reduced impurities comprising;
  a) irradiating mixture of 7-DHC alone or in combination with sterol precursors, an antioxidant and solvent in presence of the photosensitizer of Formula (I);

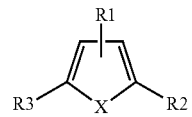

wherein;
X represents 'O' or 'S';
R1 represents a hydrogen atom or C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S;
  to obtain the mass;
  b) separating the solids, concentrating the filtrates, evaporating under vacuum to obtain crude Vitamin D3; and
  c) purifying the crude vitamin D3 of step (b) to obtain pure crystalline vitamin D3.

The sterol precursors are selected from cholesterol, phytosterol comprising (β-Sitosterol, Campesterol and Stigmasterol, or lanosterol alone or mixtures thereof.

In yet another aspect, the present invention provides an improved process for synthesis of vitamin D3 with high selectivity and reduced impurities comprising;

a) irradiating the mixture of 7-dehydrocholesterol, said photosensitizer of Formula I, an antioxidant suspended in solvent to obtain a mass;
b) evaporating the reaction mass of step (a) to obtain crude vitamin D3; and
c) purifying the crude vitamin D3 of step (b) to obtain pure crystalline vitamin D3.

In another aspect, the present invention provides an improved process for synthesis of vitamin D3 with high selectivity and reduced impurities comprising;
a) irradiating the mixture of 7-DHC with sterol precursor selected from cholesterol, phytosterol comprising of β-Sitosterol, Campesterol and Stigmasterol, or lanosterol alone or mixtures thereof; said photosensitizer of Formula I, an antioxidant suspended in solvent to obtain a mass;
b) cooling the reaction mass of step (a), filtering, concentrating to obtain a residue;
c) adding solvent to the residue of step (b), separating the solids containing Vitamin D3, 7-DHC and sterol precursor(s) for use in subsequent batches, evaporating the filtrate to obtain crude vitamin D3; and
d) purifying the crude vitamin D3 of step (c) to obtain pure crystalline vitamin D3.

The irradiation is carried out under low pressure mercury lamp as light source at a temperature in the range of 20-85° C., preferably at 40-85° C., more preferably at 60-85° C. for about 30-300 minutes, preferably for 50-280 minutes.

The photosensitizer of Formula I in the present invention is used in an amount of 0.5%-15% w/w with respect to the sterol(s) used.

The crude vitamin D3 obtained is further purified either using (i) column chromatography or (ii) by washing the mass repeatedly with aqueous acid and converting the crude vitamin D3 to its ester, crystallizing, saponifying by the process known in the art to yield pure vitamin D3 crystals.

In an aspect, the present photochemical conversion of 7-DHC alone or in combination with precursors may optionally be carried out in presence of inorganic base in an amount of 0.5% to 5% w/w of the sterol(s) used.

DESCRIPTION OF THE INVENTION

The present invention discloses an improved process for photochemical conversion of 7-dehydrocholesterol alone or in combination with sterol precursors to Vitamin D3 in presence of photosensitizer of Formula I;

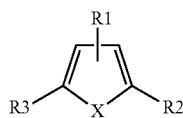

Formula I wherein;
X represents 'O' or 'S';
R1 represents a hydrogen atom or C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S;
wherein the said photosensitizer absorbs a substantial portion of the radiation to cause the photochemical conversion of 7-DHC to vitamin D3 in high yield and reduced impurities.

The samples of 7-DHC, the starting material used in the present invention is synthesized from Cholesterol isolated from either wool grease or Fish oil or Milk fat sourced from New Zealand, Chile & Europe respectively. The phytosterols are sourced from USA, Germany and Bangladesh. The other sterol Lanosterol is isolated from wool grease.

In an embodiment, the improved photochemical synthesis of vitamin D3 with high selectivity and reduced impurities comprising;
a) irradiating mixture of 7-DHC alone or in combination with sterol precursors in presence of the photosensitizer of Formula (I);

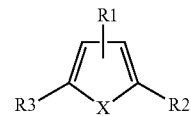

wherein;
X represents 'O' or 'S';
R1 represents a hydrogen atom or lower C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S;
to obtain the mass;
b) separating the solids, concentrating the filtrates, evaporating under vacuum to obtain crude Vitamin D3 (resin); and
c) purifying the crude vitamin D3 of step (b) to obtain pure crystalline vitamin D3.

The sterol precursors are selected from cholesterol, phytosterol comprising (3-Sitosterol, Campesterol and Stigmasterol, or Lanosterol alone or mixtures thereof in the molar concentration ranging from 0.05-0.35 moles.

In another embodiment, the photosensitizers of Formula I used in the process of present invention comprise;
i. 5-(3-pyridyl)-2,2'-Bithiophene;
ii. 2,5-Di(Pyridin-3-yl) thiophene;
iii. 2,5-diphenyl thiophene;
iv. 5-(2-Pyridyl)-2,2'-Bithiophene;
v. 5-(4-Pyridyl)-2,2'-Bithiophene;
vi. 2-Phenyl-5-(2-Pyridyl)Thiophene;
vii. 2-Phenyl-5-(3-Pyridyl)-Thiophene;
viii. 2-Phenyl-5-(4-Pyridyl)-Thiophene;
ix. 2,2'-5',2"-Terthiophene;
x. 2,5-Di(2-thienyl)Furane The 7-Dehydrocholesterol used in the present process is in the molar concentration ranging from 0.1-0.5 moles.

The photosensitizer of Formula I in the present invention is used in an amount of 0.5%-15% w/w with respect to the sterol(s) used. The photosensitizer of Formula (I) suitably absorbs the wavelength in the region of 260-300 nm emitted by low pressure mercury lamp as light source that ensures high selectivity towards conversion to vitamin D3 and reduction in formation of undesired contaminants in the irradiation reaction.

The irradiation is carried out at a temperature in the range of 20-85° C., preferably at 40-85° C., more preferably at 60-85° C. for about 30-300 minutes, preferably for 50-280 minutes.

Optionally, the pre-cooled mixture of 7-DHC alone or in combination with sterol precursors in suitable solvent is irradiated using low pressure mercury lamp wherein the heat from the mercury lamp increases the temperature of the reaction mass and the irradiation is performed for about 250-280 minutes.

The antioxidant preferably used in the present process is butylated hydroxyl toluene (BHT) and is used in catalytic amount. BHT acts as a free radical scavenger to minimize the degradation of pre-vitamin D3.

The solvent for the process is selected from polar protic or aprotic; non-polar solvent which include lower alcohols or ethers and such solvents which are inert towards the reactants and products and non-absorbing at the wavelength in which irradiation is performed. Preferably, the solvent is selected from ethanol, methanol, THF, Petroleum Ether (40-60° C.), diethyl ether, methyl-tert-butyl ether or mixtures thereof.

In an embodiment, the crude vitamin D3 obtained is further purified either using (i) column chromatography or (ii) by washing the mass repeatedly with aqueous acid and converting the crude vitamin D3 to its ester, crystallizing, saponifying by the process known in the art to yield pure vitamin D3 crystals.

In another embodiment, the present invention discloses an improved photochemical conversion of 7-Dehydrocholesterol (7-DHC) to vitamin D3 in high yield and reduced impurities comprising;
a) irradiating the mixture of 7-DHC, an antioxidant and solvent in presence of photosensitizer of Formula (I);

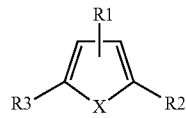

wherein;
X represents 'O' or 'S';
R1 represents a hydrogen atom or C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S;
to obtain a mass;
b) evaporating the reaction mass of step (a) to obtain crude vitamin D3; and
c) purifying the crude vitamin D3 of step (b) to obtain pure crystalline vitamin D3.

The photosensitizer of the Formula I is preferably 5-(3-Pyridyl)-2,2'-Bithiophene or 2,5-Di(Pyridin-3-yl) thiophene in an amount of 0.5%-15% w/w with respect to the sterol(s) used.

The irradiation is carried out at a temperature in the range of 20-85° C., preferably at 40-85° C., for about 120-260 minutes.

The antioxidant preferably is butylated hydroxyl toluene (BHT) which is used in catalytic amount. BHT acts as a free radical scavenger to minimize the degradation of pre-vitamin D3.

The solvent is selected from polar protic or aprotic; non-polar solvent which include lower alcohols or ethers and such solvents which are inert towards the reactants and products and non-absorbing at the wavelength in which irradiation is performed. Preferably, the solvent is selected from ethanol, methanol, THF, petroleum Ether (40-60° C.), diethyl ether, methyl-tert-butyl ether or mixtures thereof.

In a preferred embodiment, the improved photochemical synthesis of vitamin D3 with high selectivity and reduced impurities comprises;
a) irradiating the mixture of 7-DHC, BHT and solvent selected from lower alcohol or ethers in presence of photosensitizer selected from 5-(3-pyridyl)-2,2'-Bithiophene or 2,5-Di(Pyridin-3-yl) thiophene at a temperature in the range of 20-85° C. for 120-260 minutes to obtain a mass;
b) evaporating the reaction mass of step (a) to obtain crude vitamin D3 (resin); and
c) purifying the crude vitamin D3 of step (b) to obtain pure crystalline vitamin D3.

Accordingly, the mixture of 7-DHC, the inorganic base, BHT and the photosensitizer selected from 5-(3-Pyridyl)-2,2'-Bithiophene or 2,5-Di(Pyridin-3-yl) thiophene suspended in solvent selected from ethanol, methanol, THF, diethyl ether, Petroleum ether (40-60° C.) or methyl-tert-butyl ether or mixtures thereof is heated to a temperature in the range of 20-85° C., preferably at 40-85° C., and irradiated for a period of 120-260 minutes. The temperature at which the irradiation is carried out does not affect the photochemical process and the temperature is tuned to effect the solubility of 7-DHC in the solvent used.

After irradiation, the reaction mass is evaporated under vacuum and the residue is analysed on HPLC and then further purified.

In yet another embodiment, the present invention discloses an improved process for synthesis of vitamin D3 with high selectivity and reduced impurities comprising;
a) irradiating the mixture of 7-DHC with sterol precursor selected from cholesterol, phytosterol comprising β-Sitosterol, Campesterol and Stigmasterol, or lanosterol alone or mixtures thereof; an antioxidant and solvent in presence of photosensitizer of Formula (I)

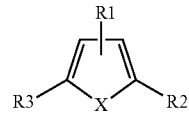

wherein;
X represents 'O' or 'S';
R1 represents a hydrogen atom or lower C1-C5 alkyl,
R2 and R3 each independently represent (un)substituted or substituted aryl group, (un)substituted or substituted naphthyl group, (un)substituted or substituted heteroaryl group having at least one heteroatom selected from N, O or S;
to obtain the mass;
b) cooling the reaction mass of step (a), separating the solids by filtration, concentrating the filtrate to obtain a residue;
c) adding solvent to the residue of step (b), separating the solids containing Vitamin D3, 7-DHC and sterol precursor for use in subsequent batches, evaporating the filtrate to obtain crude vitamin D3; and
d) purifying the crude vitamin D3 of step (c) to obtain pure crystalline vitamin D3.

7-dehydrocholesterol (7-DHC) in the present invention is used in the molar concentration ranging from 0.1-0.5 moles and the sterol precursors selected from cholesterol, phytosterol comprising β-Sitosterol, Campesterol and Stigmasterol, or lanosterol alone or mixtures thereof are used in the molar concentration ranging from 0.05-0.35 moles.

The photosensitizer of the Formula I preferably comprises 5-(3-Pyridyl)-2,2'-Bithiophene or 2,5-Di(Pyridin-3-yl) thiophene in an amount of 0.5%-15% w/w with respect to 7-DHC (i.e. pro-vitamin D3) and said sterol precursors.

The irradiation is carried out at a temperature in the range of 20-85° C., preferably at 50-85° C. for about 30-300 minutes.

The antioxidant preferably is butylated hydroxyl toluene (BHT) which is used in catalytic amount. BHT acts as a free radical scavenger to minimize the degradation of pre-vitamin D3.

The solvent is selected from polar protic or aprotic; non-polar solvent which include lower alcohols or ethers and such solvent which are inert towards the reactants and products and non-absorbing at the wavelength in which irradiation is performed. Preferably, the solvent is selected from ethanol, methanol, THF, Petroleum ether (40-60° C.), diethyl ether, methyl-tert-butyl ether or mixtures thereof.

In another preferred embodiment, the improved photochemical synthesis of vitamin D3 with high selectivity and reduced impurities comprises;

a) irradiating the mixture of 7-DHC with sterol precursor selected from cholesterol, phytosterol comprising β-Sitosterol, Campesterol and Stigmasterol or lanosterol alone or mixtures thereof; BHT and solvent selected from lower alcohol or ethers in presence of photosensitizer selected from 5-(3-pyridyl)-2,2'-Bithiophene or 2,5-Di(Pyridin-3-yl) thiophene at a temperature in the range of 20-85° C. for a period of 30-300 minutes to obtain a mass;

b) cooling the reaction mass of step (a), separating the solids by filtration, concentrating the filtrate to obtain a residue;

c) adding solvent to the residue of step (b), separating the solids containing Vitamin D3, 7-DHC and sterol precursor for use in subsequent batches, evaporating the filtrate to obtain crude vitamin D3 (resin); and d) purifying the crude vitamin D3 of step (c) to obtain pure crystalline vitamin D3.

According to the process, 7-DHC along with sterol precursor such as cholesterol, phytosterol comprising β-Sitosterol, Campesterol and Stigmasterol or lanosterol alone or mixtures thereof, BHT and the photosensitizer selected from 5-(3-Pyridyl)-2,2'-Bithiophene or 2,5-Di(Pyridin-3-yl) thiophene are dissolved in lower alcohols and irradiated by a low pressure mercury lamp at 50-85° C. for 30-300 minutes to obtain a mass. The mass is then cooled to 25-30° C. The solids separated out are filtered as first crop containing 7-DHC (40-50% of original 7-DHC used) and the sterol precursor used. The filtrate is concentrated to 20% of the original volume, cooled and the separated solids are filtered out as second crop containing 7-DHC (5-10%) along with the sterol precursor used. The filtrate is further concentrated under vacuum. To the concentrate is added the solvent selected from ethers and washed thrice with 0.1N-5N HCl followed by washing twice with 1:1 aqueous alcoholic solution. The solvent is distilled under vacuum and to the residue is added the solvent selected from ketone. The mixture is cooled to about 10° C. and the separated solids are filtered as third crop containing vitamin D3, 7-DHC (20%) and the sterol precursor (20%). All the three crops are combined and reused for subsequent batches. The filtrate is evaporated under vacuum to obtain crude vit. D3 (resin) which is further purified.

In an embodiment, the crude vitamin D3 (resin) is purified using (i) column chromatography or (ii) by washing the mass repeatedly with aqueous acid and converting the crude vitamin D3 to its ester, crystallizing, saponifying by the process known in the art to yield pure vitamin D3 crystals.

The chromatography is performed using the solvent mixture, preferably, the mixture of toluene and methyl ethyl ketone or a mixture of methylene Dichloride and n-Heptane as eluent over silica gel or alumina or 1-10% hydrated Alumina.

Alternately, the purification is carried out by washing the crude irradiated mass with aq. acid selected from 0.1-1N sulphuric acid, 0.1N-5N hydrochloric acid, 0.5N-2N Potassium hydrogen sulphate solution, 1-10% Aqueous Methane sulfonic acid solution or 5-10% aqueous p-toluene sulphonic acid solution.

Accordingly, the solution of crude vitamin D3 is washed with aq. acid to remove the base. The acidic aq. layer was then made basic ($_pH>8$) and was extracted with organic solvent to recover the photosensitizer. The organic layer is evaporated and converted to its acetate, propionate, and butyrate or nitro benzoate, crystallized, saponified and recrystallized to obtain pure vitamin D3 (Cholecalciferol). Alternately, after evaporation of the organic layer the residue is further purified by column chromatography to obtain pure vitamin D3 (Cholecalciferol).

The organic solvent is selected from aliphatic or aromatic hydrocarbons, halogenated hydrocarbons, esters, ketones and the like alone or mixtures thereof.

The step of purification either by chromatography or by washing the crude vitamin D3 with acid removes the photosensitizer, 5-(3-Pyridyl)-2,2'-Bithiophene or 2,5-Di(Pyridin-3-yl) thiophene easily which is an added advantage of the present invention.

In the alternate embodiment, the photochemical conversion of 7-DHC alone or in combination with sterol precursors of the present invention may optionally be carried out in presence of inorganic base such as alkali metal hydroxide, carbonate or bicarbonate in an amount of 0.5% to 5% w/w of the sterol(s) used.

In an embodiment, using the process of the present invention conversion of 7-dehydrocholesterol alone or in combination with suitable sterol precursor to vitamin D3 can be effected as high as 91-96% with reduced level of impurities. The invention will now be described in the following specific examples, however, it is being understood that the particulars shown are solely for purpose of illustrative discussion of preferred embodiments of the invention.

Example 1

100 gms of 7-Dehydrocholesterol (0.260M) was suspended in 2.5 L Ethanol at 28-30° C. 0.3 gms of Butylated hydroxy toluene was added at room temperature. Subsequently 8.15 gms of 5-(3-Pyridyl)-2,2'-Bithiophene was added to the reaction mass. The above reaction mass was heated to 80-85° C. and irradiated at 80-85° C. under low pressure Mercury lamp for 220 minutes. The reaction mass was evaporated under vacuum and the residue was analyzed on HPLC.

TABLE 1

| Details of Product + Impurities | % formation |
|---|---|
| Trans Vitamin D3(Impurity) | 1-1.5% |
| Lumisterol(Impurity) | 1.2-1.5% |
| Tachysterol(Impurity) | 1.4-1.75% |
| Provitamin D3(7-Dehydrocholesterol)(Raw material) | 2-3% |

TABLE 1-continued

| Details of Product + Impurities | % formation |
|---|---|
| 5-(3-Pyridyl)-2,2'-Bithiophene | 0.01% |
| Pre-Vitamin D3 + Vitamin D3(Product) | 91-93% |

The residue was dissolved in toluene and washed with 210 ml (3*70 ml) 0.1N Hydrochloric acid, 210 ml (3*70 ml) water, solvent evaporated under vacuum and the residue was purified over column chromatography to isolate the Pure crystalline Vitamin D3 using Toluene:Methyl ethyl ketone 1:99, 2:98, 3:97, 4:96 & 5:95 as a eluent over silica gel respectively.

Yield: 62 gms.
% Yield: 62%
% Assay (HPLC): 98.5-99.5%
Specific Rotation: $[\alpha]_D^{20}$: 110.2 (c=0.5, Ethanol).

Example 2

100 gms of 7-Dehydrocholesterol (0.2604 moles), 100 gms of Cholesterol (0.2590 moles), 1.5 gm of Butylated hydroxyl toluene and 1.7 gm of 5-(3-Pyridyl)-2, 2'-Bithiophene were dissolved in 2000 ml of ethanol at 75-85° C. It was then irradiated by a low pressure mercury lamp at 80-85° C. for 200 minutes. The reaction mass was cooled to 25-30° C. The solids separated out were filtered as first crop which contains 7-Dehydrocholesterol (40-50%) and Cholesterol. The filtrate was concentrated to 20% of the original volume, cooled to 20-25° C. and the separated solids were filtered as second crop that contains 7-Dehydrocholesterol (5-10%) and Cholesterol. The filtrate was again concentrated under vacuum. To the concentrate 1000 ml Methyl tert butyl ether was added and the solution was washed with 3*75 ml of 0.1 N Hydrochloric acid, followed by washing with 2*125 ml 1:1 ethanol-water and distilled under vacuum. 3500 ml of 2-Butanone (methyl ethyl ketone) was added to the residue, cooled to 10° C. and the separated solids were filtered as the third crop that contains Vitamin $D_3$ (2-5 MIU), 7-Dehydrocholesterol (20%) and Cholesterol (20%). All these first, second and third crops were combined and reused in subsequent batches.

The filtrate was then evaporated under vacuum at 40-45° C. and the crude Vitamin $D_3$ (resin) was analysed, as shown in the table below:

TABLE 2

| Sr. No | Compound | % by HPLC | Potency |
|---|---|---|---|
| 1 | Vitamin D3/Cholecalciferol + pre-Vitamin $D_3$ | 91-93% | 27-29 MIU |
| 2 | Cholesterol | 0.5-0.75% | NA |
| 3 | 7-Dehydrocholesterol | 0.5-0.75% | NA |
| 4 | Tachysterol | 0.75-1.5% | NA |
| 5 | Lumisterol | 0.5-1.5% | NA |
| 6 | 5-(3-pyridyl)-2,2'-bithiophene | 0.01% | |
| 7 | Trans Vitamin $D_3$ | 1-1.5% | NA |

The crude resin thus obtained was further purified by either of the following:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone or Methyl formate.

Purifying the crude resin by column chromatography using Silica gel or Alumina or Alumina with 2-10% water and using Toluene: 2-Butanone as a eluent.

The above irradiation process of example 1 and example 2 may be performed in Tetrahydrofuran, methyl tert-butyl ether, methanol, Petroleum Ether (40-60° C.) or Diethyl ether. After the irradiation the crude residue may be washed with 0.1-1N Sulphuric acid or 0.5-2 N Potassium hydrogen sulphate solution or 5-10% Aqueous p-Toluene sulphonic acid solution.

Example 3

163 gms of 7-Dehydrocholesterol (0.424 moles) was suspended in 4 L ethanol at 28-30° C. 0.3 gms of Butylated hydroxy toluene was added at room temperature. Subsequently 1.5 gms of 5-(3-Pyridyl)-2,2'-Bithiophene was added. The above reaction mass was heated to 80-85° C. and irradiated under low pressure mercury lamp for 210 minutes. After irradiation the reaction mass was evaporated under vacuum and the residue was analyzed on HPLC.

TABLE 3

| Details of Product + Impurities | % formation |
|---|---|
| Trans Vitamin D3(Impurity) | 0.5-1% |
| Lumisterol(Impurity) | 0.8-1% |
| Tachysterol(Impurity) | 0.8-1% |
| Provitamin Vitamin D3(7-Dehydrocholesterol)(Raw material) | 1.5-2.5% |
| 5-(3-Pyridyl)-2,2'-Bithiophene | 0.01% |
| Pre-Vitamin D3 + Vitamin D3 (Product) | 93-95% |

The reaction mass was purified over column chromatography to isolate the Pure crystalline Vitamin D3 using Toluene:Methyl ethyl ketone 1:99, 2:98, 3:97, 4:96 & 5:95 as a eluent over silica gel or Alumina respectively.

Yield: 115 gms.
% Yield: 70%
% Assay (HPLC): 98.5-99.5%
Specific Rotation: $[\alpha]_D^{20}$: 111.6 (c=0.5, Ethanol)

Example 4

82 gms of 7-Dehydrocholesterol (0.2135 moles) was suspended in 2 L methanol at 28-30° C. 0.3 gms of Butylated hydroxy toluene was added at room temperature. Subsequently 8 gms of 5-(3-Pyridyl)-2,2'-Bithiophene was added at room temperature. The mixture was heated to 65-70° C. and irradiated under low pressure mercury lamp for 240 minutes. After irradiation the reaction mass was evaporated under vacuum and the residue was analyzed on HPLC.

TABLE 4

| Details of Product + Impurities | % formation |
|---|---|
| Trans Vitamin D3(Impurity) | 0.5-1.5% |
| Lumisterol(Impurity) | 0.8-1% |
| Tachysterol(Impurity) | 0.8-1% |
| Provitamin (D3(7-Dehydrocholesterol)(Raw material) | 2-3% |

TABLE 4-continued

| Details of Product + Impurities | % formation |
| --- | --- |
| 5-(3-Pyridyl)-2,2'-Bithiophene | 0.01% |
| Pre-Vitamin D3 + Vitamin D3 (Product) | 92-94% |

The reaction mass was purified over column chromatography to isolate the Pure crystalline Vitamin D3 using Toluene:Methyl ethyl ketone 1:99, 2:98, 3:97, 4:96 & 5:95 as a eluent over silica gel or Alumina respectively.
Yield: 55 gms.
% Yield: 67%
% Assay (HPLC): 98.5-99.5%
Specific Rotation: $[\alpha]_D^{20}$: 110.8 (c=0.5, Ethanol)

Example 5

82 gms of 7-Dehydrocholesterol (0.2135 moles) was suspended in 2 L Diethyl ether at 20-25° C. 1.64 gms of Butylated hydroxy toluene was added at 20-25° C. Subsequently 1.3 gm of 5-(3-Pyridyl)-2,2'-Bithiophene was added at room temperature. The reaction mixture was cooled to 10-15° C. and irradiated under low pressure mercury lamp for 280 minutes. The reaction mass was evaporated under vacuum and the residue was analyzed on HPLC.

TABLE 5

| Details of Product + Impurities | % formation |
| --- | --- |
| Trans Vitamin D3(Impurity) | 1-1.5% |
| Lumisterol(Impurity) | 0.8-1% |
| Tachysterol(Impurity) | 0.8-1% |
| Provitamin (D3(7-Dehydrocholesterol)(Raw material) | 1.25-2.5% |
| Pre-Vitamin D3 + Vitamin D3 (Product) | 91-95% |
| 5-(3-Pyridyl)-2,2'-Bithiophene | 0.015% |

The reaction mass was then purified over column chromatography to isolate the pure crystalline Vitamin D3 using Toluene:Methyl ethyl ketone 1:99, 2:98, 3:97, 4:96 & 5:95 as a eluent over silica gel or Alumina respectively.
Yield: 52 gms
% Yield: 63%
% Assay (HPLC): 98.5-99.5%
Specific Rotation: $[\alpha]_D^{20}$: 112.3 (c=0.5, Ethanol)

Example 6

85 gms of 7-Dehydrocholesterol (0.221 moles) was suspended in 2 L Methyl tert-butyl ether at 28-30° C. 0.6 gms of Butylated hydroxy toluene was added at room temperature. Subsequently 2.3 gms of 5-(3-Pyridyl)-2,2'-Bithiophene was added at room temperature. The above reaction mass was heated to 55-58° C. and irradiated under low pressure mercury lamp for 210 minutes. After irradiation the reaction mass was evaporated under vacuum and the residue was analyzed on HPLC.

TABLE 6

| Details of Product + Impurities | % formation |
| --- | --- |
| Trans Vitamin D3(Impurity) | 1-1.5% |
| Lumisterol(Impurity) | 0.5-1% |
| Tachysterol(Impurity) | 0.8-1% |
| Provitamin (D3(7-Dehydrocholesterol)(Raw material) | 1.5-3% |

TABLE 6-continued

| Details of Product + Impurities | % formation |
| --- | --- |
| 543-Pyridyl)-2,2'-Bithiophene | 0.011% |
| Pre-Vitamin D3 + Vitamin D3 (Product) | 91-96% |

The reaction mass was purified over column chromatography to isolate the pure crystalline Vitamin D3 using Toluene:Methyl ethyl ketone 1:99, 2:98, 3:97, 4:96 & 5:95 as a eluent over silica gel or Alumina respectively.
Yield: 55 gms.
% Yield: 67%
% Assay (HPLC): 98.5-99.5%
Specific Rotation: $[\alpha]_D^{20}$: 111.1 (c=0.5, Ethanol)

Example 7

85 gms of 7-Dehydrocholesterol (0.221 moles) was suspended in 2 L THF at 28-30° C. 0.6 gms of Butylated hydroxy toluene was added at room temperature. Subsequently 1.3 gm of sodium hydroxide was added at room temperature followed by addition of 0.84 gm of 5-(3-Pyridyl)-2, 2'-Bithiophene. The above reaction mass was heated to 62-68° C. and irradiated under low pressure mercury lamp for 150 minutes. After irradiation the reaction mass was evaporated under vacuum and the residue was analyzed on HPLC.

TABLE 7

| Details of Product + Impurities | % formation |
| --- | --- |
| Trans Vitamin D3(Impurity) | 0.5-1.5% |
| Lumisterol(Impurity) | 0.5-1% |
| Tachysterol(Impurity) | 0.8-1% |
| Pro-vitamin (D3(7-Dehydrocholesterol)(Raw material) | 1.5-2.5% |
| 5-(3-Pyridyl)-2,2'-Bithiophene | 0.09% |
| Pre-Vitamin D3 + Vitamin D3 (Product) | 93-96% |

The reaction mass was purified over column chromatography to isolate the pure crystalline Vitamin D3 using Toluene:Methyl ethyl ketone 1:99, 2:98, 3:97, 4:96 & 5:95 respectively as a eluent over silica gel.
Yield: 51 gms.
% Yield: 62%
% Assay (HPLC): 98.5-99.5%
Specific Rotation: $[\alpha]_D^{20}$: 111.9 (c=0.5, Ethanol)

Example 8

163 gms of 7-Dehydrocholesterol (0.424) was suspended in 4 L Ethanol at 28-30° C. 0.5 gms of Butylated hydroxy toluene was added at room temperature. Subsequently 1.6 gms of sodium hydroxide was added at room temperature followed by addition of 15 gm of 5-(3-Pyridyl)-2,2'-Bithiophene. The above reaction mass was heated to 80-85° C. and irradiated under low pressure Mercury lamp for 210 minutes. The reaction mass was evaporated under vacuum and the residue was analyzed on HPLC.

TABLE 8

| Details of Product + Impurities | % formation |
| --- | --- |
| Trans Vitamin D3(Impurity) | 0.5-1.5% |
| Lumisterol(Impurity) | 0.8-1% |

TABLE 8-continued

| Details of Product + Impurities | % formation |
| --- | --- |
| Tachysterol(Impurity) | 0.8-1% |
| Provitamin (D3(7-Dehydrocholesterol)(Raw material) | 1.5-2.5% |
| 5-(3-Pyridyl)-2,2'-Bithiophene | 0.012% |
| Pre-Vitamin D3 + Vitamin D3 (Product) | 93-95% |

The residue was dissolved in toluene and washed with 300 ml (3*100 ml) 0.1N Hydrochloric acid, 300 ml (3*100 ml) water. The solvent was dried over anhydrous sodium sulphate and converted to its ester such as acetate or butyrate or propionate or valerate or 4-nitrobenzoate derivative by a process known in the art. The product was then crystallized, saponified by known methods/prior art adding either sodium hydroxide or potassium hydroxide and further crystallizing in methyl formate to obtain pure Vitamin D3 crystals.

Yield: 122 gms.
% Yield: 74%
% Assay (HPLC): 98.5-99.5%
Specific Rotation: $[\alpha]_D^{20}$: 110.3 (c=0.5, Ethanol).

Example 9

163 gms of 7-Dehydrocholesterol (0.424) was suspended in 4 L Ethanol at 28-30° C. 0.5 gms of Butylated hydroxy toluene was added at room temperature. Subsequently 4 gms of sodium hydroxide was added at room temperature followed by addition of 8.15 gms of 5-(3-Pyridyl)-2,2'-Bithiophene. The above reaction mass was heated to 80-85° C. and irradiated at 80-85° C. under low pressure Mercury lamp for 220 minutes. The reaction mass was evaporated under vacuum and the residue was analyzed on HPLC.

TABLE 9

| Details of Product + Impurities | % formation |
| --- | --- |
| Trans Vitamin D3 (Impurity) | 0.5-1.5% |
| Lumisterol(Impurity) | 0.8-1% |
| Tachysterol(Impurity) | 1.2-1.5% |
| Provitamin D3(7-Dehydrocholesterol)(Raw material) | 2-3% |
| 5-(3-Pyridyl)-2,2'-Bithiophene | 0.01% |
| Pre-Vitamin D3 + Vitamin D3(Product) | 92-95% |

The residue was dissolved in toluene and washed with 300 ml (3*100 ml) 0.1N Hydrochloric acid, 300 ml (3*100 ml) water, solvent evaporated under vacuum and the residue was purified over column chromatography to isolate the Pure crystalline Vitamin D3 using Toluene:Methyl ethyl ketone 1:99, 2:98, 3:97, 4:96 & 5:95 as a eluent over silica gel respectively.

Yield: 104 gms.
% Yield: 64%
% Assay (HPLC): 98.5-99.5%
Specific Rotation: $[\alpha]_D^{20}$: 109 (c=0.5, Ethanol).

Example 10

163 gms of 7-Dehydrocholesterol (0.424) was suspended in 4 L Ethanol at 28-30° C. 0.6 gms of Butylated hydroxy toluene was added at room temperature. Subsequently 25 gms of 2,5-Di(Pyridin-3-yl) thiophene was added at room temperature. The above reaction mass was heated to 80-85° C. and irradiated at 80-85° C. under low pressure Mercury lamp for 200 minutes. The reaction mass was evaporated under vacuum and the residue was analyzed on HPLC.

TABLE 10

| Details of Product + Impurities | % formation |
| --- | --- |
| Trans Vitamin D3(Impurity) | 0.5-1.5% |
| Lumisterol(Impurity) | 0.8-1.5% |
| Tachysterol(Impurity) | 0.8-1% |
| Provitamin (D3(7-Dehydrocholesterol)(Raw material) | 2-3% |
| 2,5-Di(Pyridin-3-yl) thiophene | 0.01% |
| Pre-Vitamin D3 + Vitamin D3 (Product) | 91-93% |

The reaction mass was purified over column chromatography to isolate the Pure crystalline Vitamin D3 using Toluene:Methyl ethyl ketone 1:99, 2:98, 3:97, 4:96 & 5:95 as a eluent over silica gel or Alumina respectively.

Yield: 101 gms
% Yield: 62%
% Assay (HPLC): 98.5-99.5%
Specific Rotation: $[\alpha]_D^{20}$: 111.9 (c=0.5, Ethanol)

The irradiation process illustrated in examples 3-10 may be performed in Tetrahydrofuran, methyl tert-butyl ether, methanol, Diethyl ether, Petroleum Ether (40-60° C.) as solvents. After the irradiation the crude residue may be washed with 0.1-1N Sulphuric acid or 0.5-2 N Potassium hydrogen sulphate solution, 1-10% Aqueous Methane sulfonic acid solution or 5-10% Aqueous p-Toluene sulphonic acid solution.

The purification of crude Vitamin D3 of example 10 may be performed by the purification process illustrated in example 8 and example 9.

Example 11

144 gms of 7-Dehydrocholesterol (0.375 moles), 50 gms of Cholesterol (0.129 moles), 1.5 gm of Butylated hydroxyl toluene and 40 ml of 2% Aq. Sodium hydroxide solution, 1.7 gm of 5-(3-Pyridyl)-2, 2'-Bithiophene were dissolved in 2000 ml of ethanol at 75-85° C. It was then irradiated by a low pressure mercury lamp at 80-85° C. for 200 minutes. The reaction mass was cooled to 25-30° C. The solids separated out were filtered as first crop which contains 7-Dehydrocholesterol (40-50%) and Cholesterol. The filtrate was concentrated to 20% of the original volume, cooled to 20-25° C. and the separated solids were filtered as second crop that contains 7-Dehydrocholesterol (5-10%) and Cholesterol. The filtrate was again concentrated under vacuum. To the concentrate 2000 ml Methyl tert butyl ether was added and the solution was washed with 3*100 ml of 0.1N Hydrochloric acid, followed by washing with 2*200 ml 1:1 ethanol-water and distilled under vacuum. 4500 ml of 2-Butanone (methyl ethyl ketone) was added to the residue, cooled to 10° C. and the separated solids were filtered as the third crop that contains Vitamin D3 (2-5 MIU), 7-Dehydrocholesterol (20%) and Cholesterol (20%). All these first, second and third crops were combined and reused in subsequent batches.

The filtrate was then evaporated under vacuum at 40-45° C. and the crude Vitamin $D_3$ (resin) was analysed, as shown below:

TABLE 11

| Sr. No | Compound | % by HPLC | Potency |
|---|---|---|---|
| 1 | Vitamin D₃/Cholecalciferol + pre-Vitamin D₃ | 93-94% | 27-29 MIU |
| 2 | Cholesterol | 0.5-1.5% | NA |
| 3 | 7-Dehydrocholesterol | 0.5-1.5% | NA |
| 4 | Tachysterol | 0.5-1% | NA |
| 5 | Lumisterol | 0.5-1% | NA |
| 6 | 5-(3-pyridyl)-2,2'-bithiophene | 0.01% | |
| 7 | Trans Vitamin D₃ | 1-2% | NA |

The crude resin thus obtained was further purified by either of the following:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone or Methyl formate.
2. Purifying the crude resin by column chromatography using Silica gel or Alumina or Alumina with 2-10% water and using Toluene: 2-Butanone as a eluent.
Yield: 90 gms
% Yield: 62.5%
% Assay (HPLC): 98.5-99.5%
Specific Rotation: $[\alpha]_D^{20}$: 110.8 (c=0.5, Ethanol Example 12

48 gms of 7-Dehydrocholesterol (0.124 moles), 25 gms of Phytosterol (0.0603 moles), 0.5 gm of Butylated hydroxyl toluene, 5 gms of 5-(3-Pyridyl)-2,2'-Bithiophene and 20 ml of 2% Aq. Sodium hydroxide solution were dissolved in 2500 ml of Ethanol at 75-85° C. The mixture was irradiated by a low pressure mercury lamp at 80-85° C. for 60 minutes. The reaction mass was cooled after irradiation to 35-40° C. The solids separated out were filtered as a first crop that contains 7-Dehydrocholesterol (50-60%) and Phytosterol. The filtrate was concentrated to 60% of the original volume, cooled to 25-30° C. and the separated solids were filtered as a second crop that contains 7-Dehydrocholesterol (15-20%) and Phytosterol. The filtrate was again concentrated under vacuum. 2000 ml Methyl tert butyl ether was added to the concentrate and washed with 5*150 ml of 0.1 N Hydrochloric acid followed by washing with 4*50 ml 1:1 ethanol-water mixture and distilled under vacuum. 5000 ml 2-Butanone was added to the residue, cooled to −5 to −8° C. and the separated solids were filtered as a third crop that contains Vitamin D₃ (2-4 MIU), 7-Dehydrocholesterol (15%) and Phytosterol (15%). All these first, second and third crops were combined and reused in subsequent batches. The filtrate was then evaporated under vacuum at 40-45° C. and the crude Vitamin D₃ (resin) was analysed and the results are as shown in table below:

TABLE 12

| Sr. No | Compound | % by HPLC | Potency |
|---|---|---|---|
| 1 | Vitamin D₃/Cholecalciferol + pre-Vitamin D₃ | 93-94% | 24-26 MIU |
| 2 | Phytosterol | 1-2% | NA |
| 3 | 7-Dehydrocholesterol | 1-1.5% | NA |
| 4 | Tachysterol | 0.5-1% | NA |
| 5 | Lumisterol | 0.5-1% | NA |
| 6 | 5-(3-pyridyl)-2,2'-Bithiophene | 0.017% | NA |
| 7 | Trans Vitamin D₃ | 0.5-1% | NA |

The crude resin was purified by either of the following:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone or Methyl formate.
2. Purifying the crude resin by column chromatography using Silica gel or Alumina or Alumina with 2-10% water and using Toluene: 2-Butanone as a eluent.
Yield: 26 gms
% Yield: 59%
% Assay (HPLC): 98.5-99.5%
Specific Rotation: $[\alpha]_D^{20}$: 109.9 (c=0.5, Ethanol)

Example 13

48 gms of 7-Dehydrocholesterol (0.124 moles), 100 gms of Lanosterol (0.234 moles), 1 gm of Butylated hydroxyl toluene, 6 gms of 5-(3-pyridyl)-2,2-bithiophene and 1 ml of 2% aq. sodium hydroxide solution were dissolved in 6000 ml of ethanol at 75-85° C. The mixture was irradiated by a low pressure mercury lamp at 80-85° C. for 285 minutes. The reaction mass was cooled to 30-35° C. The solids separated out were filtered as first crop which contains 7-Dehydrocholesterol (50-60%) and Lanosterol. The filtrate was concentrated to 50% of the original volume cooled to 25-30° C. and the separated solids were filtered as second crop that contains 7-Dehydrocholesterol (15-20%) and Lanosterol. The filtrate was again concentrated under vacuum. 2000 ml Methyl tert butyl ether was added and washed with 4*150 ml of 0.1 N Hydrochloric acid followed by washing with 6*50 ml 1:1 ethanol-water mixture and distilled under vacuum. 3000 ml of 2-Butanone (methyl ethyl ketone) was added to the residue, cooled to 15° C. and the separated solids were filtered to obtain third crop that contains Vitamin D₃ (15MIU), 7-Dehydrocholesterol (20%) and Lanosterol (20%). All these first, second and third crops were combined and reused in subsequent batches. The filtrate was then evaporated under vacuum at 40-45° C. and the crude Vitamin D₃ (resin) was analyzed and the results are shown in table below:

TABLE 13

| Sr. No | Compound | % by HPLC | Potency |
|---|---|---|---|
| 1 | Vitamin D₃/Cholecalciferol pre-Vitamin D₃ | 89-92% | 28-30 MIU |
| 2 | Lanosterol | 1.5-2% | NA |
| 3 | 7-Dehydrocholesterol | 1.5-2% | NA |
| 4 | Tachysterol | 1.5-2% | NA |

TABLE 13-continued

| Sr. No | Compound | % by HPLC | Potency |
|---|---|---|---|
| 5 | 5-(3-Pyridyl)-2,2'-Bithiophene | 0.015% | |
| 6 | Lumisterol | 1.5-2% | NA |

The crude resin thus obtained was further purified by either of the following:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone or Methyl Formate.
2. Purifying the crude resin by column chromatography using Silica gel or Alumina or Alumina with 2-10% water and using Toluene: 2-Butanone as eluent.

Yield: 28 gms
% Yield: 63%
% Assay (HPLC): 98.5-99.5%
Specific Rotation: $[\alpha]_D^{20}$: 111.3 (c=0.5, Ethanol)

The above irradiation process of example 11-13 may be performed in Tetrahydrofuran, methyl tert-butyl ether, methanol, Petroleum Ether (40-60° C.) or Diethyl ether or mixtures thereof. After the irradiation the crude residue may be washed with 0.1-1N Sulphuric acid or 0.5-2 N Potassium hydrogen sulphate solution or 5-10% aqueous p-Toluene sulphonic acid solution in all the examples 11-13.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

We claim:

1. A photochemical synthesis of vitamin D3 comprising:
a) irradiating 7-dehydrocholesterol (7-DHC) or a mixture of 7-DHC and a sterol precursor in the presence of a solvent and a photosensitizer of Formula (I):

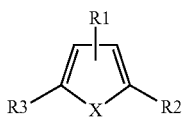

Formula I wherein;
X is O or S;
R1 is a hydrogen atom or a $C_1$-$C_5$ alkyl group,
R2 and R3 each independently represent:
an unsubstituted or substituted aryl group,
an unsubstituted or substituted naphthyl group, or
an unsubstituted or substituted heteroaryl group having at least one heteroatom selected from the group consisting of N, O, and S;
to obtain a reaction mass containing crude Vitamin D3;
b) separating the crude Vitamin D3 from the reaction mass; and
c) purifying the crude vitamin D3 to obtain crystalline vitamin D3.

2. The photochemical synthesis of claim 1, wherein the photosensitizer of Formula I is selected from the group consisting of 5-(3-pyridyl)-2,2'-bithiophene; 2,5-di(pyridin-3-yl) thiophene; 2,5-diphenylthiophene; 5-(2-pyridyl)-2,2'-bithiophene; 5-(4-pyridyl)-2,2'-bithiophene; 2-phenyl-5-(2-pyridyl)thiophene; 2-phenyl-5-(3-pyridyl)-thiophene; 2-phenyl-5-(4-pyridyl)-thiophene; 2,2'-5',2''-terthiophene; 2,5-di(2-thienyl) furane; and mixtures thereof.

3. The photochemical synthesis of claim 2, wherein the photosensitizer is 5-(3-pyridyl)-2,2'-bithiophene.

4. The photochemical synthesis of claim 2, wherein the photosensitizer is 2,5-di(pyridin-3-yl) thiophene.

5. The photochemical synthesis of claim 1, wherein the photosensitizer is present in the irradiating step in an amount of 0.5%-15% w/w, based on the weight of 7-DHC or the mixture of 7-DHC and the sterol precursor.

6. The photochemical synthesis of claim 2, wherein the photosensitizer is present in the irradiating step in an amount of 0.5%-15% w/w, with respect to 7-DHC or the mixture of 7-DHC and the sterol precursor.

7. The photochemical synthesis of claim 1, wherein the irradiating step comprises irradiating 0.1 to 0.5 moles of 7-DHC.

8. The photochemical synthesis of claim 1, wherein the irradiating step comprises irradiating the mixture of 7-DHC and the sterol precursor;
wherein the sterol precursor is selected from the group consisting of cholesterol, lanosterol, β-sitosterol, campesterol, stigmasterol, and mixtures thereof;
wherein the mixture of 7-DHC and the sterol precursor comprises 0.05 to 0.35 moles of the sterol precursor.

9. The photochemical synthesis of claim 1, wherein:
the irradiating step comprises irradiating the mixture of 7-DHC and the sterol precursor using a light source comprising a low pressure mercury lamp emitting light with a wavelength of between 260 nm and 300 nm;
the irradiating step is carried out at a temperature of 20° C. to 85° C. for a period of 30 minutes to 300 minutes; and
the photosensitizer absorbs the light with the wavelength of between 260 nm and 300 nm.

10. The photochemical synthesis of claim 1, wherein the irradiating step is carried out in the presence of a catalytic amount of butylated hydroxytoluene.

11. The photochemical synthesis of claim 1, wherein the solvent is:
selected from the group consisting of polar solvents, non-polar solvents, protic solvents, aprotic solvents, and mixtures thereof, and
non-absorbing at a wavelength used during the irradiating step.

12. The photochemical synthesis of claim 11, wherein the solvent is selected from the group consisting of alcohols and ethers.

13. The photochemical synthesis of claim 11, wherein the solvent is selected from the group consisting of ethanol, methanol, THF, diethyl ether, petroleum ether, methyl-tert-butyl ether, and mixtures thereof.

14. The photochemical synthesis of claim 1, wherein the irradiating step is carried out in the presence of an inorganic base in an amount of 0.5% to 5% w/w, based on the weight of 7-DHC or the mixture of 7-DHC and the sterol precursor.

15. A photochemical synthesis of vitamin D3, comprising:
a) irradiating a mixture comprising 7-dehydrocholesterol (7-DHC), BHT, and a solvent selected from the group consisting of lower alcohols and or ethers in the presence of a photosensitizer;
   wherein the photosensitizer is 5-(3-pyridyl)-2,2'-bithiophene or 2,5-di(pyridin-3-yl) thiophene;
   wherein the irradiating is done at a temperature in the range of 20° C. to 85° C. for a period of 120 minutes to 260 minutes to obtain a reaction mass;
b) evaporating the solvent from the reaction mass to obtain crude vitamin D3; and
c) purifying the crude vitamin D3 of step (b) to obtain pure crystalline vitamin D3.

16. The photochemical synthesis of vitamin D3 of claim 15, wherein the mixture further comprises a sterol precursor selected from the group consisting of cholesterol, β-sitosterol, campesterol, stigmasterol, lanosterol, and mixtures thereof.

17. The photochemical synthesis of vitamin D3 of claim 15, wherein the evaporating step comprises cooling the reaction mass, separating solids from the reaction mass by filtration to produce a filtrate, and concentrating the filtrate to obtain a residue comprising crude vitamin D3.

18. The photochemical synthesis of vitamin D3 of claim 16, further comprising, prior to the purifying step:
   adding a second solvent to the residue to obtain a liquid mixture,
   separating solids containing Vitamin D3, 7-DHC, and the sterol precursor from the liquid mixture by filtration to obtain a filtrate, and
   evaporating the second solvent from the filtrate to obtain crude vitamin D3.

19. The photochemical synthesis of vitamin D3 of claim 15, wherein the purifying step comprises:
   purifying the crude vitamin D3 using column chromatography;
   washing the crude vitamin D3 with aqueous acid and converting the crude vitamin D3 to a vitamin D3 ester, crystallizing the vitamin D3 ester, and saponifying the vitamin D3 ester to yield vitamin D3 crystals; or
   a combination thereof.

20. The photochemical synthesis of vitamin D3 of claim 15, wherein:
   the irradiating step is carried out using a light source comprising a low pressure mercury lamp emitting light with a wavelength of between 260 nm and 300 nm; and
   the photosensitizer absorbs the light with the wavelength of between 260 nm and 300 nm.

* * * * *